United States Patent [19]

Jaunin

[11] 4,089,875
[45] May 16, 1978

[54] PROCESS AND INTERMEDIATES FOR ISOINDOLE DERIVATIVES

[75] Inventor: Roland Jaunin, Basel, Switzerland

[73] Assignee: Hoffmann-La Roche Inc., Nutley, N.J.

[21] Appl. No.: 813,590

[22] Filed: Jul. 7, 1977

[30] Foreign Application Priority Data

Aug. 2, 1976 Austria .................................. 5704/76

[51] Int. Cl.$^2$ .................. C07C 119/14; C07D 209/44
[52] U.S. Cl. ..................................... 260/326.1; 560/35
[58] Field of Search ..................................... 260/326.1

[56] References Cited

U.S. PATENT DOCUMENTS 3,996,374  12/1976  Jaunin ................................. 260/326.1

FOREIGN PATENT DOCUMENTS 1,158,532  7/1969  United Kingdom ............ 260/325 R

OTHER PUBLICATIONS

Terada et al., Chem. Pharm. Bull., vol. 21, pp. 742-751 (1973).
Fryer, J. Het. Chem., vol. 9, pp. 747, 753 (1972).
Fryer et al., Chem. Abstracts, vol. 70, Abstract No. 106298p (1969).
Fryer et al., J. Am. Chem. Soc., vol. 88, pp. 3173-3174 (1966).

Primary Examiner—Alton D. Rollins
Attorney, Agent, or Firm—Samuel L. Welt; George M. Gould; William G. Isgro

[57] ABSTRACT

A process for the preparation of isoindole derivatives which comprises heating a compound of the formula

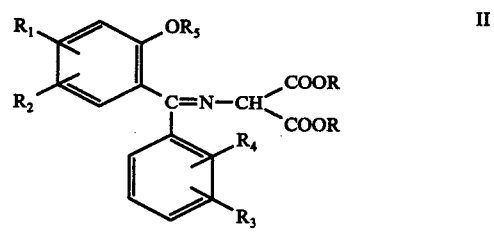

wherein $R, R_1, R_2, R_3, R_4$ and $R_5$ are hereinafter set forth, in the presence of a suitable imidazole, is described.

9 Claims, No Drawings

PROCESS AND INTERMEDIATES FOR ISOINDOLE DERIVATIVES

This is a division, of application Ser. No. 514,289 filed Oct. 11, 1974, which is a continuation-in-part of Ser. No. 463,145, filed Apr. 22, 1974, now abandoned.

BRIEF SUMMARY OF THE INVENTION

The invention comprises a process for preparing isoindole derivatives characterized by the formula

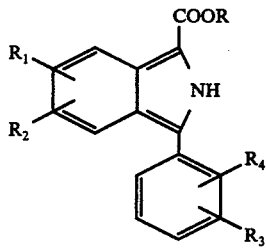

wherein R is lower alkyl and $R_1$, $R_2$, $R_3$ and $R_4$, independently, are hydrogen, halogen, lower alkyl, lower alkoxy or trifluoromethyl, by heating a malonic acid ester of the formula

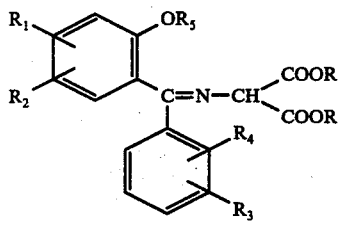

wherein $R_5$ is hydrogen, alkanoyl or aroyl, and R, $R_1$, $R_2$, $R_3$ and $R_4$ are as previously described, in the presence of a suitable imidazole.

In another aspect, the invention relates to the malonic acid esters of the formula

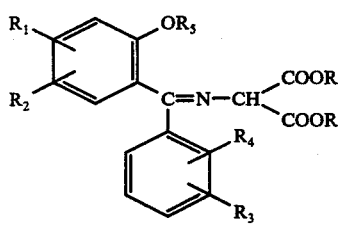

wherein R, $R_1$, $R_2$, $R_3$, $R_4$ and $R_5$ are as previously described, which are useful as intermediates in the process of the invention.

DETAILED DESCRIPTION OF THE INVENTION

The isoindole derivatives prepared according to the process of the invention are characterized by the formula

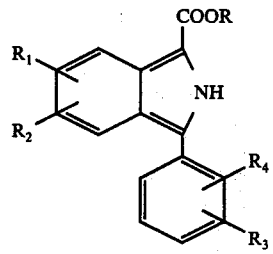

wherein R is lower alkyl and $R_1$, $R_2$, $R_3$ and $R_4$, independently, are hydrogen, halogen, lower alkyl, lower alkoxy or trifluoromethyl.

The term "lower alkyl" as utilized herein, alone or in combination, such as in "lower alkoxy," denotes a straight-chain or branched-chain saturated hydrocarbon group containing from 1 to 6 carbon atoms, for example, methyl, ethyl, propyl, isopropyl, butyl or the like. The term "halogen" denotes fluorine, chlorine, bromine and iodine. The term "alkanoyl" denotes a group derived from an aliphatic carboxylic acid containing from 1 to 6 carbon atoms, for example, formyl, acetyl, propionyl or the like. The term "aroyl" denotes a group derived from a mononuclear or polynuclear aromatic carboxylic acid in which one or more of the hydrogen atoms may independently be replaced by a substituent selected from lower alkyl, lower alkoxy or halogen. Exemplary of such aroyl groups are benzoyl, p-toluoyl, p-chlorobenzoyl, 2-naphthoyl, or the like.

In a preferred embodiment, $R_1$, $R_2$, $R_3$ and $R_4$ in formula I, independently, are hydrogen, halogen or trifluoromethyl. In an especially preferred embodiment, $R_4$ is hydrogen, $R_1$ is chlorine, fluorine or trifluoromethyl, and $R_2$ and $R_3$, independently, are hydrogen, chlorine or fluorine. R preferably is ethyl.

Particularly preferred isoindole derivatives prepared in accordance with the process of the invention are 5-chloro-3-phenylisoindole-1-carboxylic acid ethyl ester and 5-chloro-3-(p-chlorophenyl)isoindole-1-carboxylic acid ethyl ester.

The process of the invention for the preparation of the isoindole derivatives of formula I comprises heating a malonic acid ester of the formula

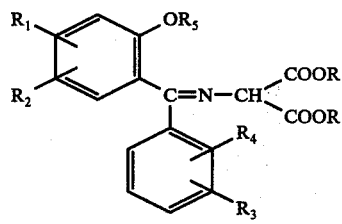

wherein $R_5$ is hydrogen, alkanoyl or aroyl, and R, $R_1$, $R_2$,
$R_3$ and $R_4$ are as previously described,
in the presence of a suitable imidazole.

Advantageously, in order to obtain high yields of the desired isoindole derivatives of formula I, malonic acid esters of formula II, wherein $R_5$ is alkanoyl or aroyl, are utilized.

Suitable imidazoles which can be utilized in the process of the invention are 2-alkyl-imidazoles, 2,4-dialkyl-imidazoles and imidazole itself. The 2-alkyl-imidazoles, and especially 2-methyl-imidazole, are preferred. The imidazole reactant is preferably utilized in a large excess. Advantageously, about equal amounts by weight of imidazole and malonic acid ester of formula II are utilized. The process can be carried out in the absence or presence of a solvent. When the process is carried out in the absence of a solvent, a malonic acid ester of formula II is conveniently heated in the presence of an imidazole at a temperature in the range of from about 90° to about 170° C., preferably in the range of from about 110° to about 150° C. When the process is carried out in the presence of a solvent, there can be used as the solvent an aprotic neutral solvent, for example, toluene, xylene, tetralin, dioxane, cyclohexanone, dimethylformamide, or the like. The heating of the reaction mixture can conveniently be carried out at the same temperatue range as that adopted when the process is conducted in the absence of a solvent. Preferably, the process is carried out either in the absence of a solvent or utilizing xylene as the solvent. The heating time depends on the temperature at which the reaction is carried out and generally lies in the range of from about 1 hour to 36 hours. When the process is carried out at the preferred temperature range of from about 110° to about 150° C., then the heating time is in the range of from about 1 hour to 18 hours, particularly in the range of from about 1 hour to about 5 hours.

The malonic acid ester starting materials of formula II are novel and also form part of the invention. The compounds of formula II can be prepared by reacting a benzophenone derivative of the formula

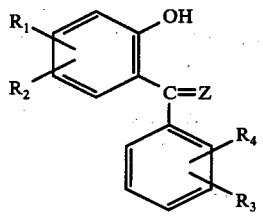

III wherein Z is oxygen or the group NH and $R_1$, $R_2$, $R_3$ and $R_4$ are as previously described,
with an aminomalonic acid ester in a known manner.

Since the imines of formula III are generally more reactive than the corresponding ketones, imines are preferably utilized. Conveniently, the reaction is carried out in an inert organic solvent, for example, an alcohol, such as ethanol, propanol or butanol, or an aromatic hydrocarbon, such as benzene or toluene, at a temperature in the range of from about 60° to about 150° C., preferably in the range of from about 75° to about 120° C. When a solvent having a boiling point in the preferred temperature range of the reaction is utilized, the reaction is conveniently carried out at the reflux temperature of the reaction mixture. When an alcohol is used as the solvent, then it will be appreciated that the alcohol utilized should correspond to the alcohol giving rise to the ester group in the aminomalonic acid ester utilized, otherwise a transesterification could occur. Since the aminomalonic acid ester is preferably utilized in the form of an acid addition salt, the reaction is preferably carried out in the presence of an acid acceptor, which conveniently can be a base, for example, a tertiary amine, such as triethylamine, or the like, or pyridine.

A malonic acid ester of formula II, wherein $R_5$ is hydrogen, can be converted, if desired, in a known manner into a corresponding malonic acid ester of formula II wherein $R_5$ is alkanoyl or aroyl, by reaction under anhydrous conditions with an acylating agent, for example, an acid anhydride, such as acetic anhydride or the like, or an acid halide, such as benzoyl chloride or the like, if desired in the presence of an acid acceptor, for example, pyridine, at a temperature in the range of from about 20° to about 100° C. A malonic acid ester of formula II wherein $R_5$ is hydrogen need not be isolated prior to the acylation.

The benzophenone derivatives of formula III are known compounds or can be prepared in an analogous manner to the known benzophenone derivatives.

The isoindole derivatives of formula I are known compounds and are intermediates for the preparation of isoindoles which are substituted at the nitrogen with a basic moiety and which posses anorectic activity.

The following Examples further illustrate the invention. All temperatures are in degrees centigrade unless otherwise mentioned.

EXAMPLE 1

Preparation of 5-chloro-3-phenylisoindole-1-carboxylic acid ethyl ester

100 G. of [(2-acetoxy-5-chloro-α-phenylbenzyliden-)amino]malonic acid diethyl ester and 100 g. of 2-methyl-imidazole are charged into a sulfonation flask and mixed at room temperature for 15 minutes while gassing with argon. The stirrer is then disconnected and the flask immersed in an oil-bath preheated to 140° C. The mixture is left to melt with occasional agitation (about 10–20 minutes), and, from the time when a homogeneous liquid is obtained, the flask is held for a further 1 hour in the oil-bath at 140° C. After about 15 minutes, a brisk gas evolution can be observed, there being finally obtained a semi-solid brownish mass. After removing the oil-bath and cooling the contents of the flask to about 80° C., 800 ml. of absolute ethanol are added in one portion and the suspension obtained is boiled at reflux while stirring for 10 minutes. It is then cooled and left to stand in an ice-bath for 2 hours. The yellow-colored crude product which crystallizes out is filtered off under suction, washed with two 150 ml. portions of ice-cold absolute ethanol and then with two 200 ml. portions of absolute ether and dried in the dark under reduced pressure at 60° C. Yellowish crystals of melting point 206°–209° C. (decomposition) are obtained. For purification, these crystals are boiled in 400 ml. of chloroform for 15 minutes and, after cooling in an ice-bath for 1 hour, filtered off under suction, washed with two 125 ml. portions of absolute ether and dried in the dark under reduced pressure at 60° C. There are obtained 41.6 g. of yellowish felt-like crystals of 5-chloro-3-phenylisoindole-1-carboxylic acid ethyl ester, having a melting point of 208°–210° C. (decomposition). The starting material can be prepared as follows:

A suspension of 115.3 g. of 5-chloro-2-hydroxybenzophenone in 1000 ml. of absolute ethanol is charged into a sulfonation flask. A rapid stream of dry ammonia is then introduced without cooling for 2 hours, the benzophenone being completely dissolved after about 15–20 minutes and the imine formed beginning to crystallize out somewhat later. The mixture is then concentrated to a volume of about 200 ml. and left to stand in an ice-bath for 1 hour.

The product is filtered off under suction washed with two 100 ml. portions of ice-cold absolute ethanol and dried at 45° C. in vacuo. Yellow-orange crystals of 5-chloro-2-hydroxy-benzophenone imine of melting point 129°–131° C. are obtained. The ethanolic mother liquor is concentrated to about 100 ml. and cooled. The crystallizate is filtered off under suction, washed with two 25 ml. portions of ice-cold absolute ethanol and dried at 45° C. in vacuo. An additional amount of 5-chloro-2-hydroxy-benzophenone imine, having a melting point of 128°–131° C. is obtained.

A suspension of 57.8 g. of 5-chloro-2-hydroxy-benzophenone imine in 375 ml. of absolute ethanol is charged into a sulfonation flask and treated successively at room temperature with 79.2 g. of aminomalonic acid diethyl ester hydrochloride and 53.5 ml. of triethylamine. The mixture is then boiled at reflux for 4 hours, strong evolution of ammonia gas taking place. The mixture is then evaporated to dryness. The residue is treated immediately with 200 ml. of acetic anhydride and boiled at reflux for 30 minutes. After standing overnight, the suspension obtained is concentrated to dryness and the residue treated with 1l. of ice-water. This mixture is shaken for 2 hours on a rotary shaker, the separated product becoming completely solid. It is filtered off under suction, washed with four 300 ml. portions of water and dissolved in 1000 ml. of methylene chloride. The aqueous layer is separated and the methylene chloride solution washed successively with three 200 ml. portions of water, two 150 ml. portions of 2-N sodium carbonate solution and two 100 ml. portions of saturated sodium chloride solution, dried over sodium sulfate, filtered and evaporated. The residue is triturated with 500 ml. of n-heptane and cooled in an ice-bath. The light-brown product which crystallizes out is filtered off under suction, washed with two 100 ml. portions of low-boiling petroleum ether and dried at 40° C. in vacuo. The crude product obtained is recrystallized from 250 ml. of absolute ethanol. There are obtained almost colorless crystals of [(2-acetoxy-5-chloro-2-phenylbenzyliden)amino]malonic acid diethyl ester having a melting point of 85°–87° C.

EXAMPLE 2

Preparation of 5-chloro-3-phenylisoindole-1-carboxylic acid ethyl ester

A suspension of 5 g. of [(2-benzoyloxy-5-chloro-α-phenylbenzyliden)amino]malonic acid diethyl ester in 25 ml. of xylene is treated with 5 g. of 2-methyl-imidazole and the mixture boiled at reflux for 4 hours. The mixture is then cooled to about 80° C., 25 ml. of ethanol are added, and the resulting mixture is heated to reflux while stirring for a further 10 minutes. After standing in an ice-bath for 2 hours, the product which crystallizes out is filtered off under suction and washed with a small amount of ethanol and ether. There are obatined 1.6 g. of 5-chloro-3-phenylisoindole-1-carboxylic acid ethyl ester in the form of yellowish crystals, having a melting point of 208°–210° C. (decomposition).

The starting material can be prepared as follows:

A suspension of 9.2 g. of 5-chloro-2-hydroxy-benzophenone imine in 60 ml. of ehtanol is treated with 12.6 g. of aminomalonic acid diethyl ester hyrochloride and 5.0 ml. of pyridine and the mixture boiled at reflux for 1 hour while stirring. The mixture is then concentrated to dryness under reduced pressure and the residue partitioned between toluene and water. The organic phase is washed with water, briefly dried over sodium sulfate and evaporated to dryness. The residual oily residue crystallizes upon trituration with hexane. There is obtained [(5-chloro-2-hydroxy-α-phenylbenzyliden)amino] malonic acid diethyl ester, having a melting point of 55°–56° C. Recrystallization from ethanol yields gold-yellowish leaflets having the same melting point.

A solution of 7.8 g. of [(5-chloro-2-hydroxy-α-phenylbenzyliden)amino] malonic acid diethyl ester in 15 ml. of pyridine is treated at 10°–15° C. with 3.5 ml. of benzoyl chloride. The mixture is stirred at room temperature for 1 hour and then poured on to 150 ml. of ice-water. The separated oil product is extracted with ehter and the organic phase washed with water, then with 2-N sodium carbonate solution and finally with water. After drying over sodium sulfate and evaporation of the solvent, the oily residue is triturated with hexane, crystallization setting in. There is obtained [(2-benzoyloxy-5-chloro-α-phenylbenzyliden)amino] malonic acid diethyl ester in the form of colorless crystals, having a melting point of 108°–110° C. Recrystallization from ethanol increases the melting point to 109°–111° C.

EXAMPLE 3

Preparation of 3-(4-chlorophenyl)-6-methoxy-isoindole-1-carbxoylic acid ethyl ester 5 G. of {[2-hydroxy-4-methoxy-α-(4-chlorophenyl)-benzyliden]-amino} malonic acid diethyl ester are heated with 5 g. of 2-methyl-imidazole at 140° C. for 1 hour according to the procedure described in Example 1. After treatment with ethanol, the crude product obtained is purified by crystallization from ethyl acetate, there being obtained 0.75 g. of 3-(4-chlorophenyl)-6-methoxy-isoindole-1-carboxylic acid ethyl ester in the form of yellowish crystals having a melting point of 234°–237° C. (decomposition). The starting material can be prepared as follows:

A suspension of 132 g. of 4'-chloro-2-hydroxy-4-methoxy-benzophenone in 500 ml. of methanol is cooled to −20° C. in a 2l. shaking autoclave and treated with 120 ml. of liquid ammonia. The mixture is then shaken at 120° C. for 20 hours under a nitrogen atmosphere. After cooling, the yellow crude product is filtered off under suction and washed with a small amount of methanol. There is obtained 4'-chloro-2-hydroxy-4-methoxy-benzophenone imine, having a melting point of 210°–212° C., which can be used in the next step without further purification. An analytical sample is obtained by recrystallization from methanol and has a melting point of 212°–214° C.

10.5 G. of 4'-chloro-2-hydroxy-4-methoxy-benzophenone imine in 60 ml. of ethanol is reacted with 12.6 g. of aminomalonic acid diethyl ester hydrochloride and 5.0 ml. of pyridine in accordance with the procedure described in Example 2. After a single recrystallization of the crude product from ethanol, there is obtained {[2-hydroxy-4-methoxy-α-(4-chlorophenyl)benzyliden]-amino}malonic acid diethyl ester, having a melting point of 73°–75° C.

EXAMPLE 4

Preparation of 3-(4-chlorophenyl)-5-methyl-isoindole-1-carboxylic acid ethyl ester 4.5 G. of }[2-acetoxy-5-methyl-α-(4-chlorophenyl)-benzyliden]-amino}malonic acid diethyl ester are reacted at 140° C. for 1 hour with 4.5 g. of 2-methylimidazole in a manner analogous to that described in Example 1. After recrystallization of the crude product from ethanol, there are obtained 1.2 g. of 3-(4-chlorophenyl)-5-methylisoindole-1-carboxylic acid ethyl ester in the form of yellowish felt-like crystlas. having a melting point of 195°–197° C. (decomposition).

The starting material {[2-acetoxy-5-methyl-α-(4-chlorophenyl)benzyliden]-amino}malonic acid diethyl easter (colorless crystals from heptane, melting point 82°–84° C), can be prepared as described in Example 1 from 4'-chloro-2-hydroxy-5-methylbenzophenone via 4'-chloro-2-hydroxy-5-methyl-benzophenone imine (orange crystals from ethanol, melting point 134°–136° C).

EXAMPLE 5

Preparation of 5-chloro-3-phenylisoindole-1-carboxylic acid methyl ester 7.0 G. of [(2-benzoyloxy-5-chloro-α-phenylbenzyliden)amino]malonic acid dimethyl ester are reacted at 140° C. for 1 hour with 7.0 g. of 2-methyl-imidazole according to the procedure described in Example 1. After cooling the contents of the flask to 60° C., 30 ml. of methanol are added, the suspension obtained is boiled at reflux for 10 minutes and subsequently left to stand in an ice-bath for 2 hours. There is obtained 1.0 g. of yellow-greenish felt-like crystals of 5-chloro-3-phenylisoindole-1-carboxylic acid methyl ester, having a melting point of 208°–210° C. (decomposition). The methanolic mother liquor is concentrated to dryness and the residue chromatographed on 300 g. of silica gel using chloroform for the elution; there being thus obtained an additional amount (1.3 g.) of 5-chloro-3-phenylisoindole-1-carboxylic acid methyl ester, having a melting point of 208°–210° C. (decomposition). The total yield amounts to 53%.

The starting material, [(2-benzoyloxy-5-chloro-α-phenylbenzyliden)amino] malonic acid dimethyl ester (colorless crystals from methanol, melting point 127°–129° C.), can be prepared in a manner analogous to that described in Example 2 from 5-chloro-2-hydroxybenzophenone imine and aminomalonic acid dimethyl ester hydrochloride via [(5-chloro-2-hydroxy-α-phenylbenzyliden)amino]malonic acid dimethyl ester (yellow crystals from methanol, melting point 94°–96° C.).

Example 6

Preparation of 5-chloro-3-(3,4-dichlorophenyl)-isoindole-1-carboxylic acid ethyl ester A suspension of 2.0 g. of {[2-benzoyloxyl-5-chloro-α-(3,4-dichlorophenyl)benzyliden]-amino} malonic acid diethyl ester in 10 ml. of xylene is treated with 2.0 g. of 2-methylimidazole and the mixture is boiled at reflux for 4 hours. The mixture is then concentrated to dryness under reduced pressure and the solid residue obtained boiled with 10 ml. of ethanol. After cooling in an ice-bath, there is obtained 0.55 g. of yellow-greenish felt-like crystals of 5-chloro-3-(3,4-dichlorophenyl)-isoindole-1-carboxylic acid ethyl ester, having a melting point of 187°–189° C. (decomposition). Recrystallization from ethyl acetate does not increase the melting point.

The starting material, {[2-benzoyloxy-5-chloro-α-(3,4-dichlorophenyl)benzyliden]-amino} malonic acid diethyl ester (colorless crystals from ethanol, melting point 102°–103° C), can be prepared from the corresponding 2-hydroxy-benzophenone derivative in an analogous manner to that described in Example 2 via 3',4 ,5-trichloro-2-hydroxybenzophenone iminine (orange crystals from ethanol, melting point 118°–119°C) and {[5-chloro-2-hydroxy-α-(3,4-dichlorophenyl)benzyliden]amino}malonic acid diethyl ester (yellowish crystals from melting point 77°–79° C).

5-Chloro-6-methyl-3-phenyliosindole-1-carboxylic acid ethyl ester [yellow crystals form ethyl acetate, melting point 234°–236° C. (decomposition)] is manufactured in an analogous manner to that described in the first paragraph of this Example starting from [(2-benzoyloxy-5-chloro-4-methyl-α-phenylbenzyliden)-amino] malonic acid diethyl ester (colorless crystals from ethanol, melting point 94°–96° C). This diethyl ester can be prepared from the corresponding 2-hydroxy-benzophenone derivative in an analogous manner to that described in Example 2 via 5-chloro-2-hydroxy-4-methyl-benzophenone imine (orange crystals from ethanol, melting point 129°–130° C) and [(5-chloro-2-hydroxy-4-methyl-α-phenylbenzyliden)amino] malonic acid diethyl ester (yellow crystals from ethanol, melting point 100°–101° C).

5-Fluoro-3-phenylisoindole-1-carboxylic acid ethyl ester [green-yellowish crystals, melting point 184°–186° C. (decomposition)] is manufactured in an analogous manner to that described in the first paragraph of this Example starting from [(2-benzoyloxy-5-fluoro-α-phenylbenzyliden)amino]malonic acid diethyl ester (colorless crystals from ethanol, melting point 76°–78° C.). This diethyl ester can be prepared from the corresponding 2-hydroxy-benzophenone derivative in an analogous manner to that described in Example 2 via 5-fluoro-2-hydroxy-benzophenone imine (orange crystals from ethanol, melting point 100°–101° C.) and [(5-fluoro-2-hydroxy-α-phenylbenzyliden)-amino] malonic acid diethyl ester (yellow crystals from ethanol, melting point 59'–60° C).

EXAMPLE 7

Preparation of 5-chloro-3-phenylisoindole-1-carboxylic acid ethyl ester

A suspension of 2.0 g. of [(2-acetoxy-5-chloro-α-phenylbenzyliden)amino]malonic acid diethyl ester in 10 ml. of xylene is treated with 2.0 g. of 2-ethyl-4-methylimidazole and the mixture boiled at reflux for 6 hours. The temperature is then allowed to drop to 80° C., 10 ml. of ethanol are added and the resulting mixture is heated to reflux for 5 minutes while stirring. The mixture is then left to stand in an ice-bath for 4 hours and the crystallized product is subsequently filtered off and washed with ethanol and ether. There is obtained 0.73 g. of 5-chloro-3-phenylisoindole-1-carboxylic acid ethyl ester having a melting point of 208°–210 20 C. (decomposition).

I claim:

1. A process for the preparation of isoindoles of the formula wherein R is lower alkyl and $R_1$, $R_2$, $R_3$ and $R_4$, independently, are hydrogen, halogen, lower alkyl, lower alkoxy or trifluoromethyl, which comprises heating a malonic acid ester of the formula

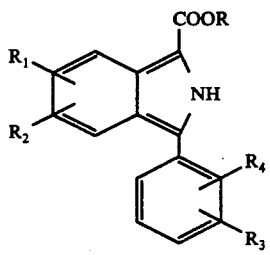

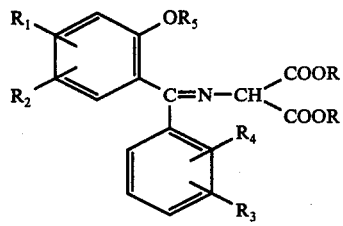

wherein $R_5$ is hydrogen, alkanoyl or aroyl, and R, $R_1$, $R_2$, $R_3$ and $R_4$ are previously described, in the presence of a suitable imidazole.

2. A process in accordance with claim 1, wherein the suitable imidazole is imidazole, 2-alkyl-imidazole or 2,4-dialkyl-imidazole.

3. A process in accordance with claim 2, wherein the suitable imidazole is 2-methyl-imidazole.

4. A process in accordance with claim 1, wherein the heating is carried out in the absence of a solvent.

5. A process in accordance with claim 1, wherein the heating is carried out in the presence of a solvent.

6. A process in accordance with claim 5, wherein the solvent is an aprotic neutral solvent.

7. A process in accordance with claim 6, wherein the aprotic neutral solvent is toluene, xylene, tetralin, dioxane, cyclohexanone or dimethylformamide.

8. A process in accordance with claim 1, wherein $R_1$, $R_2$, $R_3$ and $R_4$, independently, are hydrogen, halogen, or trifluoromethyl.

9. A process in accordance with claim 1, wherein $R_4$ is hydrogen, $R_1$ is chlorine, fluorine or trifluoromethyl, $R_2$ and $R_3$, independently, are hydrogen, chlorine or fluorine, and R is ethyl.

* * * * *